United States Patent [19]

Lotsof

[11] Patent Number: 5,152,994
[45] Date of Patent: * Oct. 6, 1992

[54] RAPID METHOD FOR INTERRUPTING OR ATTENUATING POLY-DRUG DEPENDENCY SYNDROMES

[76] Inventor: Howard S. Lotsof, 46 Oxford Pl., Staten Island, N.Y. 10301

[*] Notice: The portion of the term of this patent subsequent to Feb. 12, 2002 has been disclaimed.

[21] Appl. No.: 531,100

[22] Filed: May 31, 1990

[51] Int. Cl.$^5$ .................. A01N 43/46; A61K 31/55; A61K 9/08; A61K 9/48
[52] U.S. Cl. .................................. 424/436; 424/451; 424/463; 424/464; 514/214; 514/810; 514/811; 514/812; 514/813
[58] Field of Search ............... 514/810, 811, 812, 813, 514/214; 424/401, 436, 451, 463, 464

[56] References Cited

U.S. PATENT DOCUMENTS

| | | | |
|---|---|---|---|
| 4,499,096 | 2/1985 | Lotsoff | 514/214 |
| 4,587,243 | 5/1986 | Lotsoff | 514/214 |
| 4,857,523 | 8/1989 | Lotsoff | 514/214 |

OTHER PUBLICATIONS

"Effect of ibogaine on naloxone-precipitated withdrawal syndrome in chronic morphine-dependent rats", Dzoljic et al, Arch. Int. Pharmacodyn Ther., 294, 64-70, 1988.

Primary Examiner—Thurman K. Page
Assistant Examiner—Carlos Azpuru
Attorney, Agent, or Firm—Howard C. Miskin

[57] ABSTRACT

The administration to a poly-drug addict of ibogaine, ibogaine, tabernanthine, alkaloids in the family of apocynaceae, or their non-toxic salts have been discovered to interrupt the physiological and psychological aspects of poly-drug dependency (heroin, cocaine, alcohol, nicotine, caffeine, amphetamine, desoxyephedrine or methadone in combinations thereof). A single treatment or series of treatments may be effective for one to eighteen months or longer. Treatment consists of the oral or rectal administration of ibogaine, ibogamine, tabernanthine or their salts or derivatives in dosage ranges of 1 mg/kg to 60 mg/kg.

7 Claims, No Drawings

RAPID METHOD FOR INTERRUPTING OR ATTENUATING POLY-DRUG DEPENDENCY SYNDROMES

BACKGROUND OF THE INVENTION

The present invention relates generally to improvements in the treatment of poly-drug dependency and addiction and relates particularly to an improved method for interrupting the physiological and psychological aspects of detoxification and withdrawal associated with combined addictions in which heroin, methadone, cocaine, amphetamine, caffeine, nicotine, desoxyephedrine and ethol alcohol may be used in various combinations, concurrently.

While previous patents have been granted for the treatment of narcotic dependency (U.S. Pat. No. 4,449,096), cocaine and amphetamine abuse (U.S. Pat. No. 4,587,243) and alcohol dependency (U.S. Pat. No. 4,857,523) there has heretofore been no general treatment for multiple addiction syndromes. The majority of drug users are now poly-drug addicted and researchers in the area of drug dependency treatment recognize the pharmacological differences and behavioral uniqueness of such dependencies.

In the treatment for poly-drug addiction syndromes, there are no known medical procedures for general application. Those treatments which are applied are directed toward specific dependencies within the poly-drug spectrum and have substantial associated problems in which the patient will be re-addicted to another narcotic and/or suffer substantial discomfort during the detoxification treatment procedure or require daily injections or administrations in a chronic modality of other addicting or mood altering substances.

HISTORICAL BACKGROUND

Ibogaine, ibogamine and tabernanthine are among at least 12 alkaloids found in the Tabernanthe iboga plant of West Africa. The Gabonese as well as, Africans in other countries on that continent have used the iboga alkaloids in the Bwiti religion and Mbiri medical societies, principally, during the last century. Ethnographic studies have been performed by two principal specialists: Otto Gollnhofer and James W. Fernandez. Gollnhofer's works include "Rits of Passage in the Bwiti Initiation Society among the Mitsogo: The chewing of Iboga, Doctoral Thesis, 3red cycle, Rene Descartes University, Paris V, 1974 as well as, "Iboga, an African Psychotropic Agenent; Psychotrope vol. 2, No. 3, 1985, Montreal, Que. and Ritual Uses of Iboga in Gabon, Ibid, Vol. 2, No. 3, 1985. Fernandez's book, one of the few in English, "Bwiti—An Ethnography of Religious Imagination in Africa" (Princeton Press, 1982) offers an in depth view of the Bwiti religion among the Fang peoples of Gabon.

One of the first European references to the drugs was made by Professor Baillon at the Mar. 6th, 1889 session of the Linnaen Society in Paris during which he described samples obtained by Griffon de Bellay from Gabon and the French Congo.

Early isolation and identification of ibogaine was accomplished by Dybowski and Landrin (Compt. rend. ac. sc. 133:748, 1901); Haller and Heckel (ibid. 133:850); Lambert and Heckel (ibid. 133:1236 and Landrin (Bull. sc. pharm. 11:1905).

Interest in the drugs seemed to lie fallow until research was picked up by Raymond-Hamet and his associate E. Rothlin. Raymond-Hamet published the "Effects Of Ibogaine On The Isolated Rabbit Uterus" in 1938 (Compt. rend. soc. biol. 127:592-4). Raymond-Hamet continued to study the drug for a period of 22 years. He singularly published 9 papers: Pharmacological Action Of Ibogaine (Arch. intern. pharmacodynamie, 63:27-39, 1939), Two Physiological Properties Common To Ibogaine And Cocaine (Compt. rend. soc. biol. 133:426-9, 1940), Ibogaine and Ephedrine (Ibid. 134:541-4, 1940), Difference Between Physiological Action of Ibogaine And That Of Cocaine ((Ibid. 211:285-8, 1940), Mediate And Intermediate Effects Of Ibogaine On The Intestine (Compt. rend. soc. biol. 135:176-79, 1941), Pharmacological Antagonism Of Ibogaine (Compt. rend. 212:768-771, 1941), Some Color Reactions Of Ibogaine (Bull. soc. chim. biol. 25:205-10, 1943), Sympathicosthenic Action Of Ibogaine On The Vessels Of The Dog's Paw (Compt. rend. 233:757-58, 1946), and Interpretation Of The Ultraviolet Absorption Curves Of Ibogaine And Tabernanthine (Ibid. 229:1359-61, 1949).

A good source of botanical, pharmacological and toxicological data coming out of this historical period can be found in Jean Delourme-Houde's Thesis (Etude de l'Iboga, University of Paris, 1943). Still another researcher Vincent, D. began his work on ibogaine by a collaboration with Sero, I.: Inhibiting Action Of Tabernanthe Iboga on Serum Cholinesterase (Compt. rend. soc. biol. 136:612-14, 1942). Vincent participated in the publication of Five other papers: The Ultraviolet Absorption Spectrum Of Ibogaine (Brustier, B., Vincent, D. & Sero, I., Compt. rend. 216:909-911, 1943), Detection Of Cholinesterase Inhibiting Alkaloids (Vincent, D. & Beaujard, P, Ann. pharm. franc. 3:22-26, 1945), The Cholinesterase Of The Pancreas: Its Behavior In The Presence Of Some Inhibitors In Comparison With The Cholinesterases Of Serum And Brain (Vincent, D. & Lagreau, P., Bull. soc. chim. biol. 31:1043-45. 1949); and two papers which he and Ramond-Hamet worked on together: Action Of Some Sympathicosthenic Alkaloids On The Cholinesterases (Compt. rend. soc. biol. 150:1384-86, 1956) and On Some Pharmacological Effects Of Three Alkaloids Of Tabernanthe Iboga, Baillon: Ibogaine, Iboluteine And Tabernathine (Compt. rend. soc. biol. 154:2223-27, 1960).

Another of the French chemists to provide substantial information on ibogaine has been Dr. Robert Goutarel, considered by two generations of French chemists to be the "father of ibogaine research". Goutarel's work includes, Structure of Ibogaine (Goutarel, R.; Janot, M. & M.; Mathys, F and Prelog, V.: Compt. rend, ac. sc., 237:1718, 1953), "Research on Some Alkaloids and Their Relations with the Metabolism of Tryptophane and Dihydroxyphenylalanine; (Thesis for doctorate of Science, Paris, 1954) nd U.S. Pat. No. 2,813,873 (Nov., 19, 1957) Derivatives of the ibogaine alkaloids.

The structure of ibogaine was also investigated by Dickel et al (J.A.C.S. 80:123, 1958). The first total synthesis was cited by Buchi et al. (J.A.C.S. 87:2073, 1965) and (Ibid. 88, 3099, 1966).

In 1956 Salmoiraghi and Page elucidated ibogaine's relations to serotonin (J. Pharm. & expt. ther. 120(1):20-25, 1957.9). About the same time J. A. Schneider published three important papers. The first, Potentiation Action Of Ibogaine On Morphine Analgesia was done in collaboration with Marie McArthur (Experiential 12:323-24, 1956). The second was Neuropharmacological Studies Of Ibogaine: An Indole Alkaloid With Central Stimulant Properties (Schneider, J. A. & Sigg, E. B., Ann. of NY acad. of sciences. 66:765-76, 1957) and third was An Analysis Of The Cardiovascular Action Of Ibogaine HCl (Schneider, J. A. & Rinehard, R. K., Arch. int. pharmacodyn. 110:92-102, 1957).

Ibogaine's stimulant properties were further investigated by Chen and Bohner in A Study Of Central Nervous System Stimulants (J. Pharm & expt. ther. 123(3):212-215, 1958). Gershon and Lang published A Psychological Study Of Some Indole Alkaloids (Arch. intern. pharmacodynamie, 135:31-56, 1962).

R. D. Bunag evaluated certain aspects of the relationship between ibogaine and Substance P (Bunag, R. D., Walaszek, E. J., The Cardiovascular Effects Of Substance P In The Chicken, Ann. NY Acad. sci. 104(1):437-48, 1963).

Claudio Naranjo reported on the effects of ibogaine on human subjects in his paper, Psychotherapeutic Possibilities Of New Fantasy-Enhancing Drugs (Clinical Toxicology 2(2):209-224, June 1969).

Dhahir, H. I. published a good review of the pharmacology and toxicology of ibogaine in his Doctoral Thesis, A Comparative Study Of The Toxicity Of Ibogaine And Serotonin (University Microfilms International 71-25-341, Ann Arbor, Mich.). The paper gives an overview of much of the work accomplished with ibogaine.

Additional studies of interest include: The Effects Of Some Hallucinogens On Aggressiveness Of Mice And Rats (Kostowski et al., Pharmacology 7:259-63, 1972), Cerebral Pharmacokinetics Of Tremor-Producing Harmala And Iboga Alkaloids (Zetler et al., Pharmacology 7(4):237-248, 1972), High Affinity 3H-Serotonin Binding To Caudate: Inhibition By Hallucinogenic And Serotonergic Drugs (Whitaker, P. & Seeman, P., Psychopharmacology 59:1-5, 1978), Selective Labeling Of Serotonin Receptors by d-(3H) Lysergic Acid Diethylamide In Calf Caudate (Proc. natl. acad. sci., USA 75(12):5783-87, Dec. 1978) and A Common Mechanism Of Lysergic Acid, Indolealkylamine And Phenethylamine Hallucinogens: Serotonergic Mediation Of Behavioral Effects In Rats (Sloviter, R. et al., J. Pharm. & expt. ther. 214(2):231-38, 1980). The most current work has been performed by Dzoljic, M. R.; Dzoljic E. D. and Kaplan, C. D. (Effect of Ibogaine on Naloxone-Precipitated Withdrawal Syndrome in Chronic Morphine dependent Rats, Arch. Int. Pharmacodyn., 294:64-70, 1988.)

SUMMARY OF THE INVENTION

It is the principal object of the present invention to provide an improved method for the treatment of poly-drug dependency.

Another object of the present invention is to provide an improved method for lessening the physiological and psychological aspects of poly-drug deprivation and withdrawal in the addict/abuser.

Still another object of the present invention is to provide a method of the above nature characterized by its high degree of success, the absence of the great pain and discomfort accompanying earlier treatments, the ease and convenience of application, the absence of undesirable or persistent side effects, the long term effectiveness of the treatment and its acceptance to the addict population.

The above and other objects of the present invention will become apparent from a reading of the following description which sets forth preferred embodiments thereof.

A feature of the present invention is based on the discovery that alkaloids of the family Apocynaceae and their therapeutically active derivatives and salts, particularly for example, ibogaine, ibogamine and tabernanthine hydrochloride, tannate, tartrate and other non-toxic salts of those alkaloids, possess the unexpected unique ability to interrupt poly-drug dependency.

For the purpose of definition, the poly-drug dependency and abuse syndrome consists of the pharmacology imposed by such use and all of the symptomology demonstrated by a drug abuser concurrently addicted to, or using, alcohol, heroin, methadone, cocaine, caffeine, amphetamine, desoxyephedrine or nicotine in one or more combinations thereof.

A single treatment or series of treatments of ibogaine, ibogamine, tabernanthine or their salts or derivatives in doses ranging from 1 mg/kg to 60 mg/kg, administered orally or rectally interrupted the use heroin, cocaine, alcohol, nicotine, methadone, caffeine, amphetamines or desoxyephedrine in various combinations for one to eighteen months or longer.

In the administration of acceptable dosage forms, any of a variety of preparations may be compounded, for example: capsules, tablets, pills, powder, solutions, injections or suppositories, etc. In addition to the active agent, there may be present additional substances used in the manufacture of pharmaceutical preparations such as binders, fillers and other inert ingredients.

The advantage of this invention is that it allows for the rapid interruption of physical withdrawal symptoms associated with poly-drug dependency as well as, removing the patient's craving to continue poly-drug use. The patients status, after treatment, if craving is not totally interrupted, allows successful reversal or modification of drug seeking behavior via various adjunct techniques in the majority of cases, as the underlying psycopathology is usually unmasked with the acute interruption of drug dependency by the primary administration.

The following examples are given by way of illustration of the present and improved method of treating poly-drug abuse or dependency and are not intended to limit the scope of the present invention. The examples are part of a study of nine subjects, seven of whom where successfully treated.

EXAMPLE 1

Subject, age 43, was treated for cocaine dependency. Subject was additionally smoking two or more packs of filter cigarettes per day. Subject was administered a single dose of 15 mg/kg of ibogaine. Subject suffered no nicotine withdrawal and has not smoked cigarettes or used cocaine for more than 24 months, at which time tracking ceased.

EXAMPLE 2

Subject, age 34, female was treated for heroin dependency. The subject was smoking 1¼ grams of heroin per day for three months, had been addicted without interruption for over a year and had a fourteen year history of heroin use. Subject was concurrently smoking one and a half packs of filter cigarettes per day. Acute interruption of heroin addiction was successfully completed with the administration of 15 mg/kg of ibogaine. Cigarette smoking continued, but diminished over a thirty day period at which time the subject ceased to smoke cigarettes and maintained this state for sixty days, at which time tracking was discontinued.

EXAMPLE 3

Subject, male, age 22 was a heroin/methadone addict concurrently drinking alcohol on a daily basis. Subject had been on methadone for nine years except for a one year stay in a correctional institution. Methadone use had been at a 65 mg/day level for twelve months. Lifetime heroin use had been for fifteen years with a current level of ¼ gram per day supplementing methadone use. A single treatment with 15 mg/kg of ibogaine interrupted heroin and methadone use. Subject did not go through physical narcotic withdrawal. This individual attempted heroin use once after his treatment at which time he stated he no longer liked heroin and did not go back to heroin use. Alcohol use which had consisted of daily, continuous drinking of beer and wine with a lifetime history of alcohol abuse of twelve years was reduced by fifty to one hundred percent per day. Subject left country three weeks after treatment with no further tracking possible.

EXAMPLE 4

Subject, male, age 42 was addicted to alcohol, cocaine and heroin. Use of alcohol consisted of drinking distilled spirits on a daily basis with a lifetime history of drinking for twenty years. Heroin use was at a level of ninety dollars per day for the last thirty days with a lifetime history of heroin use of ten years. Cocaine use was twenty-five out of the last thirty days at levels of thirty dollars per day. Lifetime use for cocaine was four years. A single dose of ibogaine (15 mg/kg) completely interrupted heroin and cocaine use and diminished alcohol use by fifty to eighty percent on a daily basis. Subject has been heroin and cocaine free for two months.

EXAMPLE 5

Subject, male, age 26 was using thirty to sixty dollars worth of heroin per day and smoking ¼ ounce of cocaine base per day. A single treatment with ibogaine HCl (20 mg/kg) interrupted heroin and cocaine use completely with no physical withdrawl. Subject had used heroin an average of twenty-five days a month and cocaine base twenty days a month. Lifetime history of heroin use was three years. Lifetime use of cocaine was ten years. Subject has reamined cocaine free for two months. Subject was heroin free for one month and then began using heroin once or twice a week. Subject considered his cocaine addiction and not his heroin addiction as a problem prior to treatment.

While there have been described preferred embodiments of the present invention, it is apparent that numerous alterations, omissions and additions may be made without departing from the spirit thereof.

I claim:

1. The method of treating poly-drug dependency comprising (one) administering to (one) a subject dependent on at least two drugs selected from the group consisting of heroin, cocaine, alcohol, caffeine, amphetamine, desoxyephedrine, nicotine, methadone and opiate narcotics a dosage comprising ibogaine, ibogamine, tabernanthine or a therapeutically active physiologically acceptable compound of ibogaine, ibogamine, tabernanthine or a mixture thereof in an amount within the range of 1–60 mg/kg weight of said subject.

2. The method of claims 1 wherein said compound is a non-toxic salt of ibogaine, ibogamine, tabernanthine or a base thereof.

3. The method of claim 1 wherein said dosage comprises ibogaine, ibogamine, tabernanthine or one or more non-toxic salts of thereof or a mixture thereof.

4. The method of claim 3 wherein said dosage comprises a member of a group consisting of ibogaine, tabernanthine and ibogamine on a form selected from the group consisting of a free base, a hydrochloride, tartrate, tannate or hydrobromide salt.

5. A method of claim 3 or 4 wherein a plurality of said dosages are administered, the administration of successive dosages being separated by a plurality of days or parts of days.

6. The method of claim 3 or 4 wherein said dosage is administered orally or by suppository or rectal infusion.

7. The method of claim 5 wherein said dosage is administered orally or by suppository or rectal infusion.

* * * * *

UNITED STATES PATENT AND TRADEMARK OFFICE
CERTIFICATE OF CORRECTION

PATENT NO. : 5,152,994
DATED : October 6, 1992
INVENTOR(S) : Howard S. Lotsof

It is certified that error appears in the above-indentified patent and that said Letters Patent is hereby corrected as shown below:

On the title page, under "References Cited", change "Lotsoff" to --Lotsof-- (three occurrences).

On the title page, under "Abstract", line 2, change "Ibogaine" to --ibogamine--.

Column 2, claim 1, line 15, delete two occurrences of "(one)".

Signed and Sealed this

Twenty-third Day of November, 1993

Attest:

BRUCE LEHMAN

Attesting Officer    Commissioner of Patents and Trademarks